United States Patent
Frisken (10) Patent No.: US 12,161,411 B2
(45) Date of Patent: Dec. 10, 2024

(54) HYPERSPECTRAL APPARATUS AND METHOD

(71) Applicant: Cylite Pty Ltd, Notting Hill (AU)

(72) Inventor: Steven James Frisken, Vaucluse (AU)

(73) Assignee: Cylite Pty Ltd, Notting Hill (AU)

( * ) Notice: Subject to any disclaimer, the term of this patent is extended or adjusted under 35 U.S.C. 154(b) by 836 days.

(21) Appl. No.: 17/273,329

(22) PCT Filed: Sep. 4, 2019

(86) PCT No.: PCT/AU2019/050943
§ 371 (c)(1),
(2) Date: Mar. 4, 2021

(87) PCT Pub. No.: WO2020/047594
PCT Pub. Date: Mar. 12, 2020

(65) Prior Publication Data
US 2021/0330184 A1  Oct. 28, 2021

Related U.S. Application Data (60) Provisional application No. 62/727,492, filed on Sep. 5, 2018.

(51) Int. Cl.
*A61B 3/10* (2006.01)
*A61B 5/00* (2006.01)
(Continued)

(52) U.S. Cl.
CPC .......... *A61B 3/1025* (2013.01); *A61B 5/0071* (2013.01); *G01J 3/0208* (2013.01);
(Continued)

(58) Field of Classification Search
CPC ......... A61B 3/102; A61B 5/0066; A61B 3/14; A61B 3/0025; A61B 3/1225; A61B 3/12;
(Continued)

(56) References Cited

U.S. PATENT DOCUMENTS

| | | | |
|---|---|---|---|
| 8,908,277 | B2 | 12/2014 | Pesach |
| 9,618,452 | B2 | 4/2017 | Chen |
| 2006/0192971 | A1 | 8/2006 | Carver |
| 2006/0273255 | A1 | 12/2006 | Volkov et al. |
| 2009/0154886 | A1 | 6/2009 | Lewis |

(Continued)

FOREIGN PATENT DOCUMENTS

| | | | |
|---|---|---|---|
| CN | 104568777 A | | 4/2015 |
| CN | 105324649 A | | 2/2016 |

(Continued)

OTHER PUBLICATIONS

Translation of Chinese Office Action received in corresponding Chinese Application No. 201980056673 dated Aug. 4, 2023.

(Continued)

*Primary Examiner* — Brandi N Thomas
(74) *Attorney, Agent, or Firm* — MATTINGLY & MALUR, PC (57) ABSTRACT

The present invention relates to a hyperspectral apparatus and method. One aspect of the invention provides an apparatus for analyzing a sample. The apparatus comprises a light source configured to generate a broadband input irradiance field. The apparatus also comprises a structured light generator for converting the input irradiance field into a structured illumination field including an array of beamlets. An optical system projects the structured illumination field onto a region of the sample such as the retina. A spectrometer is configured to spectrally analyze a portion of light that is reflected, backscattered or fluoresced from the region of the sample. A processor is operatively associated with the spectrometer and configured to generate a hyperspectral image comprising two or more en-face images of the region of the eye. The en-face images include spectral response information of the sample from each beamlet of the structured illumination field.

16 Claims, 5 Drawing Sheets

(51) Int. Cl.
  *G01J 3/02* (2006.01)
  *G01J 3/28* (2006.01)
  *G01J 3/42* (2006.01)
  *G01J 3/44* (2006.01)
  *G02B 27/09* (2006.01)

(52) U.S. Cl.
  CPC ............ *G01J 3/0289* (2013.01); *G01J 3/2803* (2013.01); *G01J 3/42* (2013.01); *G01J 3/4406* (2013.01); *G01J 3/4412* (2013.01); *G02B 27/0955* (2013.01); *A61B 3/102* (2013.01); *G01J 2003/425* (2013.01)

(58) Field of Classification Search
  CPC ................ A61B 3/1025; A61B 3/0008; A61B 2018/00642; A61B 5/0075; A61B 3/1015; A61B 5/7257; A61B 18/20; A61B 2017/00057; A61B 5/0086; A61B 3/103; A61B 5/0084; A61B 2562/0266; A61B 5/0059; A61B 5/0068; A61B 5/0093; A61B 5/318; A61B 5/42; A61B 8/12; A61B 8/5261; A61B 1/046; A61B 18/201; A61B 18/203; A61B 18/22; A61B 2017/00061; A61B 2017/00101; A61B 2017/00128; A61B 2018/00017; A61B 2018/00565; A61B 2018/00577; A61B 2018/00601; A61B 2018/0066; A61B 2018/00672; A61B 2018/00678; A61B 2018/00684; A61B 2018/00702; A61B 2018/00708; A61B 2018/0072; A61B 2018/00732; A61B 2018/00738; A61B 2018/00744; A61B 2018/00761; A61B 2018/00767; A61B 2018/00785; A61B 2018/00791; A61B 2018/00809; A61B 2018/00833; A61B 2018/00863; A61B 2018/00886; A61B 2018/2035; A61B 2018/20351; A61B 2018/20359; A61B 2018/20553; A61B 3/10; A61B 5/4836; A61B 5/6852; A61B 1/0638; A61B 1/0684; A61B 3/1241; A61B 5/0035; A61B 5/6803; A61B 2562/0242; A61B 3/1005; A61B 3/1233; A61B 5/0082; A61B 2562/046; A61B 2576/02; A61B 3/0083; A61B 3/0091; A61B 3/107; A61B 3/113; A61B 3/145; A61B 5/004; A61B 5/0071; A61B 5/02007; A61B 5/4088; A61B 8/10; A61B 8/42; A61B 8/4209; A61B 8/4245; A61B 8/4281; A61B 8/4416; A61B 8/4461; A61B 8/5207; A61B 1/227; A61B 18/02; A61B 18/04; A61B 18/1492; A61B 18/24; A61B 3/13; A61B 5/026; A61B 5/14546; A61B 5/14555; A61B 5/14558; A61B 5/6817; A61B 3/00; A61B 3/0041; A61B 3/18; A61B 5/00; A61B 5/0064; A61B 5/0073; A61B 5/0215; A61B 5/02154; A61B 5/0261; A61B 5/441; A61B 5/445; A61B 5/726; A61B 5/7267; A61B 5/7275; A61B 5/742; A61B 1/000094; A61B 1/000096; A61B 1/0005; A61B 10/0233; A61B 2090/064; A61B 2090/3735; A61B 2090/3937; A61B 2090/3941; A61B 2217/005; A61B 2562/0233; A61B 3/0058; A61B 3/112; A61B 3/117; A61B 3/152; A61B 3/16; A61B 5/0077; A61B 5/0095; A61B 5/1072; A61B 5/1172; A61B 5/14552; A61B 5/4222; A61B 5/489; A61B 5/7203; A61B 5/7225; A61B 5/7425; A61B 6/027; A61B 6/032; A61B 6/06; A61B 6/4007; A61B 6/4014; A61B 6/4028; A61B 6/4241; A61B 6/4266; A61B 6/4429; A61B 6/482; A61B 6/484; A61B 6/5205; A61B 6/5282; A61B 6/54; A61B 6/542; A61B 6/544; G01B 9/02091; G01B 9/02044; G01B 9/02004; G01B 9/0203; G01B 9/02014; G01B 11/22; G01B 2290/20; G01B 2290/70; G01B 9/02083; G01B 9/02069; G01B 9/02015; G01B 9/02047; G01B 9/02007; G01B 9/02028; G01B 9/02054; G01B 9/02055; G01B 11/0675; G01B 9/02029; G01B 9/02038; G01B 9/02067; G01B 9/04; G01B 9/02; G01B 9/02041; G01B 2290/45; G01B 9/02058; G01B 9/02077; G01B 9/02027; G01B 9/0205; G01B 9/0209; G01B 9/02002; G01B 9/02005; G01B 9/0201; G01B 9/02011; G01B 9/02019; G01B 9/02043; G01B 2290/65; G01B 9/02037; G01B 9/02075; G01B 11/2441; G01B 11/2513; G01B 9/02003; G01B 9/02012; G01B 9/02045; G01B 9/02057; G01B 9/02068; G01B 9/02079; G01B 9/02084; G01B 9/02087; G01B 9/02088; G01B 11/24; G01B 11/26; G01B 11/27; G01B 5/0037; G01B 9/00; G01B 9/02009; G01B 9/02048; G01B 9/02063; G01B 9/02072; G01B 9/021; G02B 27/1013; G02B 21/0056; G02B 21/0028; G02B 26/105; G02B 21/00; G02B 21/008; G02B 26/06; G02B 26/08; G02B 27/0068; G02B 21/0076; G02B 21/06; G02B 21/367; G02B 21/245; G02B 21/26; G02B 21/361; G02B 27/1006; G02B 6/102; G02B 7/28; G02B 21/0064; G02B 27/126; G02B 6/0006; G02B 6/4214; G02B 6/4268; G02B 6/4286; G02B 2006/12159; G02B 21/365; G02B 27/0955; G02B 3/005; G02B 6/29352; G02B 19/0014; G02B 19/0052; G02B 27/0911; G02B 27/0916; G02B 27/0966; G02B 27/0977; G02B 27/30; G02B 6/003; G02B 6/12007; G02B 6/2813; G02B 2005/1804; G02B 21/002; G02B 21/0032; G02B 21/004; G02B 21/14; G02B 27/00; G02B 27/1086; G02B 27/46; G02B 27/48; G02B 3/14; G02B 5/20; G02B 6/29349; G02B 6/4215; G02B 13/0095; G02B 17/0896; G02B 2006/1215; G02B 2006/12164; G02B 21/0012; G02B 21/16; G02B 21/22; G02B 21/36; G02B 6/12004; A61F 9/008; A61F 2009/0087; A61F 2009/00872; A61F 9/00825; A61F 2009/00851; A61F 2009/00846; A61F 2009/00848; A61F 2009/00853; A61F 9/009; A61F 2009/00887; A61F 2/16; A61F 2/1613; A61F 2/1637; A61F 2/1648; A61F 2/1662; A61F 2/1683; A61F 2002/16901; A61F 2009/00859; A61F 2009/0088; A61F 2009/00897; A61F 2220/0016; A61F 9/00; A61F 9/007; A61F 9/00754; A61F 9/00812; A61F 2009/00842; A61F 2009/00844; A61F 2009/00855; A61F 2009/00889; A61F 9/00802

See application file for complete search history.

(56) References Cited

U.S. PATENT DOCUMENTS

| | | | |
|---|---|---|---|
| 2016/0135679 | A1 | 5/2016 | Frisken et al. |
| 2016/0327776 | A1 | 11/2016 | Tsia et al. |
| 2017/0176338 | A1 | 6/2017 | Wu et al. |
| 2018/0242838 | A1* | 8/2018 | Sarunic ............ G02B 21/0076 |
| 2019/0226991 | A1* | 7/2019 | Sinha ................. G02B 21/16 |

FOREIGN PATENT DOCUMENTS

| | | |
|---|---|---|
| CN | 105352923 A | 2/2016 |
| CN | 107850530 A | 3/2018 |
| WO | 03/046607 A1 | 6/2003 |
| WO | 2009/098516 A2 | 8/2009 |
| WO | 2017205857 A1 | 11/2017 |
| WO | 2018000036 A1 | 1/2018 |

OTHER PUBLICATIONS

Extended European Search Report received in corresponding European Application No. 19858221.5 dated May 2, 2022.

Kim et al 'Multiphoton microscopy based on multianode photomultiplier tubes', Optics Express 15(18), 11658-11678 (2007).

Ben Ami et al 'Spatial and spectral characterization of human retinal pigment epithelium fluorophore families by ex vivo hyperspectral autofluorescence imaging', Translational Vision Science & Technology 5(3), Article 5 (2016).

Dwight et al 'Lenslet array tunable snapshot imaging spectrometer (LATIS) for hyperspectral fluorescence microscopy', Biomedical Optics Express 8(3), 1950-1964 (2017).

* cited by examiner

HYPERSPECTRAL APPARATUS AND METHOD

RELATED APPLICATIONS

The present application claims priority from U.S. Provisional Patent Application No. 62/727,492 filed on 5 Sep. 2018, the contents of which are incorporated herein by reference.

FIELD OF THE INVENTION

The present invention relates to apparatus and methods for interrogating a sample and, in particular, to apparatus and methods for performing hyperspectral imaging and fluorescence spectroscopy of a sample. While some embodiments will be described herein with particular reference to that application, it will be appreciated that the invention is not limited to such a field of use, and is applicable in broader contexts.

BACKGROUND OF THE INVENTION

Any discussion of the background art throughout the specification should in no way be considered as an admission that such art is widely known or forms part of common general knowledge in the field.

Hyperspectral imaging of the human eye can be used to extract both spectral and spatial information about the eye. However, current techniques typically involve point-scanning systems, which have long acquisition times and suffer from motion blur artifacts. Furthermore, current systems are typically not confocally limited and therefore capture stray light from different sample locations.

Another limitation of existing systems is cost. Hyperspectral imaging systems require spatially coherent broadband optical sources to operate efficiently. Such optical sources are typically expensive.

Retinal Auto Fluorescence (AF) is a contrast indicator that is useful in identifying the build up or concentration of certain molecules in the retina, in particular in the retinal pigment epithelium (RPE). Blue light excited AF of the retina preferably uses confocal detection rather than a fundus photo to identify the AF signal to prevent the large signal from other parts of the eye from swamping the image. There are commercially available instruments that can provide AF measurements using blue light excitation, which is particularly valuable in lipofuscin contrast, an important molecule related to the aging and health of the RPE layer and hence the photoreceptors.

There is also interest in identifying molecules such as collagen from other parts of the eye such as the sclera and lens.

Alternatively, information about the nature of the fluorescence can be obtained from the lifetime of the AF signal, but this requires very high speed processing and only point by point imaging. This limits the area of the eye that can be scanned in a time that is comfortable for the patient. An alternative to lifetime measurements is to distinguish on the basis of the spectrum of the fluorescence and/or absorption. However, only limited work has been done in this field and many of the studies have been ex-vivo.

The inventor has identified that it would be advantageous to have improved apparatus and methods for more efficiently and accurately performing hyperspectral imaging and fluorescence spectroscopy of an eye.

SUMMARY OF THE INVENTION

It is an object of the present invention to overcome or ameliorate at least one of the disadvantages of the prior art, or to provide a useful alternative.

In accordance with a first aspect of the present invention there is provided an apparatus for analyzing a sample, the apparatus comprising:
- a light source configured to generate an input irradiance field having a wavelength band consisting of a plurality of wavelengths;
- a structured light generator for converting the input irradiance field into a structured illumination field comprising an array of beamlets;
- an optical system for projecting the structured illumination field onto a region of the sample, including angularly encoding the beamlets such that each beamlet is projected onto a position of the sample corresponding to the encoded angle;
- a spectrometer comprising a two-dimensional sensor array configured to spectrally analyze a portion of light that is reflected, backscattered or fluoresced from the region of the sample; and
- a processor operatively associated with the spectrometer, the processor including:
  - a spectral mapping module configured to map, based on a predefined mapping function, positions on the sensor array to a two-dimensional position on the sample and a wavelength of the light within a plurality of predefined wavelength bins; and
  - a hyperspectral image generator configured to generate a hyperspectral image from sensor signals of the sensor array and the predefined mapping function, the hyperspectral image comprising two or more en-face images of the region of the sample, the two or more en-face images including spectral response information of the sample from each beamlet of the structured illumination field.

Preferably, the structured light generator is configured to convert the input irradiance field into a structured illumination field comprising a two-dimensional array of beamlets.

In some embodiments, the light source is spatially incoherent.

In some embodiments, the optical system includes means for translating the structured illumination field relative to the sample. In one embodiment, the means for translating the structured illumination field relative to the sample includes a tiltable mirror.

In some embodiments, the optical system includes a dispersive element for angularly dispersing each of the beamlets into an elongated band of beamlet spectral components corresponding to each of the plurality of wavelengths. The optical system preferably includes a lens relay disposed, in use, between the dispersive element and the sample to project the beamlet spectral components onto the sample at a position that is dependent on both the original beamlet position in the array of beamlets and the wavelength of the beamlet spectral component. The beamlet spectral components of different beamlets preferably overlap on the region of the sample such that multiple wavelengths are imaged by the spectrometer at each point in an area of overlap on the region of the sample.

The spectral response information preferably includes a reflectance power spectrum corresponding to each point on the region of the sample.

In some embodiments, the dispersive element is mechanically moveable to be removed from the optical path. In some embodiments, the dispersive element is interchangeable with a non-dispersive optical directing element.

In some embodiments, the processor is configured to divide the wavelengths corresponding to the elongated band of beamlet spectral components into the wavelength bins, wherein wavelengths within a wavelength bin are designated as originating from a common position on the sample and wavelengths of different wavelength bins are designated as originating from different positions on the sample.

In some embodiments, each of the angularly encoded beamlets projected onto the region of the sample include each of the plurality of wavelengths.

In some embodiments, the spectral response information includes a fluorescence spectrum corresponding to a response of the sample to each beamlet of the structured illumination field.

In some embodiments, the structured light generator includes a beamlet generating device having a two-dimensional array of optical power elements, the beamlet generating device being positioned such that, in use, the input irradiance field is incident onto the array of optical power elements to generate a two-dimensional array of at least partially collimated beamlets. Preferably, the beamlet generating device includes a first microlens array with the optical power elements being microlenses.

In some embodiments, the structured light generator further includes:
  a first optical power device for spatially converging the array of at least partially collimated beamlets to a predefined width at a convergence plane; and
  an aperture disposed at the convergence plane, the aperture having a diameter smaller than a diameter of the array of at least partially collimated beamlets at the convergence plane.

In one embodiment, the first optical power device is a high numerical aperture lens. In another embodiment, the first optical power device is a gradient index lens.

Preferably, the structured light generator further includes:
  a second optical power device having a predefined focal length and being disposed at a distance equal to the predefined focal length from the convergence plane, the second optical power device generating a near-collimated beam comprising a group of at least partially overlapping beamlets; and
  a second microlens array having a two-dimensional array of microlenses and being positioned to receive the near-collimated beam and generate a two-dimensional array of beamlets for illuminating the sample.

In some embodiments, the apparatus includes an aperture array positioned to confocally project the light that is reflected, backscattered or fluoresced from the region of the sample into the spectrometer, the aperture array having a pitch corresponding to the array of beamlets.

In some embodiments, the light source is configured to generate an input irradiance field having a plurality of wavelength bands, each consisting of a corresponding plurality of wavelengths. Preferably, a first wavelength band is selected from the ultraviolet A, violet, blue or green regions of the electromagnetic spectrum. Preferably, a second wavelength band is in the near infrared region of the electromagnetic spectrum.

In some embodiments, the optical system includes a multiplexing element for multiplexing the plurality of wavelength bands together. Preferably, the multiplexing element is a volume phase grating. The volume phase grating is preferably configured to spatially disperse the plurality of wavelengths from one of the wavelength bands while maintaining the plurality of wavelengths of another wavelength band in a spatially confined state.

In some embodiments, the apparatus includes a reference arm and a power splitting element configured to direct a portion of the optical power of the structured illumination field along the reference arm and the remainder of the optical power of the structured illumination field to the sample.

In certain embodiments, a length of the reference arm is selectively adjustable so as to select a wavelength of coherence to be imaged by the spectrometer.

Preferably, the apparatus is configured for analyzing a sample comprising an eye.

In accordance with a second aspect of the present invention there is provided a system for generating a structured illumination field, the system comprising:
  a spatially incoherent light source configured to generate an input irradiance field having a predefined spectral output;
  a beamlet generating device having a two-dimensional array of optical power elements, the beamlet generating device being positioned such that the input irradiance field is incident onto the array of optical power elements to generate a two-dimensional array of at least partially collimated beamlets;
  a first optical power device for spatially converging the array of at least partially collimated beamlets to a predefined width at a convergence plane;
  a second optical power device having a predefined focal length and being disposed at a distance equal to the focal length from the convergence plane, the second optical power device generating a near-collimated beam comprising a group of at least partially overlapping beamlets; and
  a microlens array having an array of microlenses and being positioned to receive the near-collimated beam and generate a structured illumination field comprising an array of beamlets.

The microlens array preferably comprises a two-dimensional array of microlenses such that the structured illumination field comprises a two-dimensional array of beamlets.

In some embodiments, the system comprises an aperture disposed at the convergence plane, the aperture having a diameter smaller than the predefined width of the array of at least partially collimated beamlets at the convergence plane.

In one embodiment, the first optical power device is a high numerical aperture lens. In another embodiment, the first optical power device is a gradient index lens.

Preferably, the beamlet generating device includes a microlens array with the optical power elements being microlenses.

In accordance with a third aspect of the present invention there is provided a method of analyzing a sample, the method comprising the steps of:
  generating, from an input irradiance field having a wavelength band consisting of a plurality of wavelengths, a structured illumination field comprising an array of beamlets;
  projecting the structured illumination field onto a region of the sample, including angularly encoding the beamlets such that each beamlet is projected onto a position of the sample corresponding to the encoded angle; and
  spectrally analyzing a portion of the light that is reflected, backscattered or fluoresced from the region of the sample using a two-dimensional sensor array, the spectral analyzing including:
    mapping, based on a predefined mapping function, positions on the sensor array to a two-dimensional position on the sample and a wavelength of the light within a plurality of predefined wavelength bins; and generating a hyperspectral image from sensor signals of the sensor array and the predefined mapping function, the hyperspectral image comprising two or more en-face images of the region of the sample, the two or more en-face images including spectral response information of the sample from each beamlet of the structured illumination field.

Preferably, the structured illumination field comprises a two-dimensional array of beamlets.

In accordance with a fourth aspect of the present invention there is provided an article of manufacture comprising a computer usable medium having a computer readable program code configured to operate the apparatus of the first aspect.

In accordance with a fifth aspect of the present invention there is provided an article of manufacture comprising a computer usable medium having a computer readable program code configured to implement the method of the third aspect.

BRIEF DESCRIPTION OF THE DRAWINGS

Preferred embodiments of the disclosure will now be described, by way of example only, with reference to the accompanying drawings in which.

DETAILED DESCRIPTION

System Overview

The present invention will be described with reference to the application of studying the physiology and morphology of an eye in-vivo, such as in ophthalmology. However, it will be appreciated that the invention may be applied in broader non-ocular applications such as skin inspection, food analysis and high-resolution microscopy.

Figures 1A, 1B:
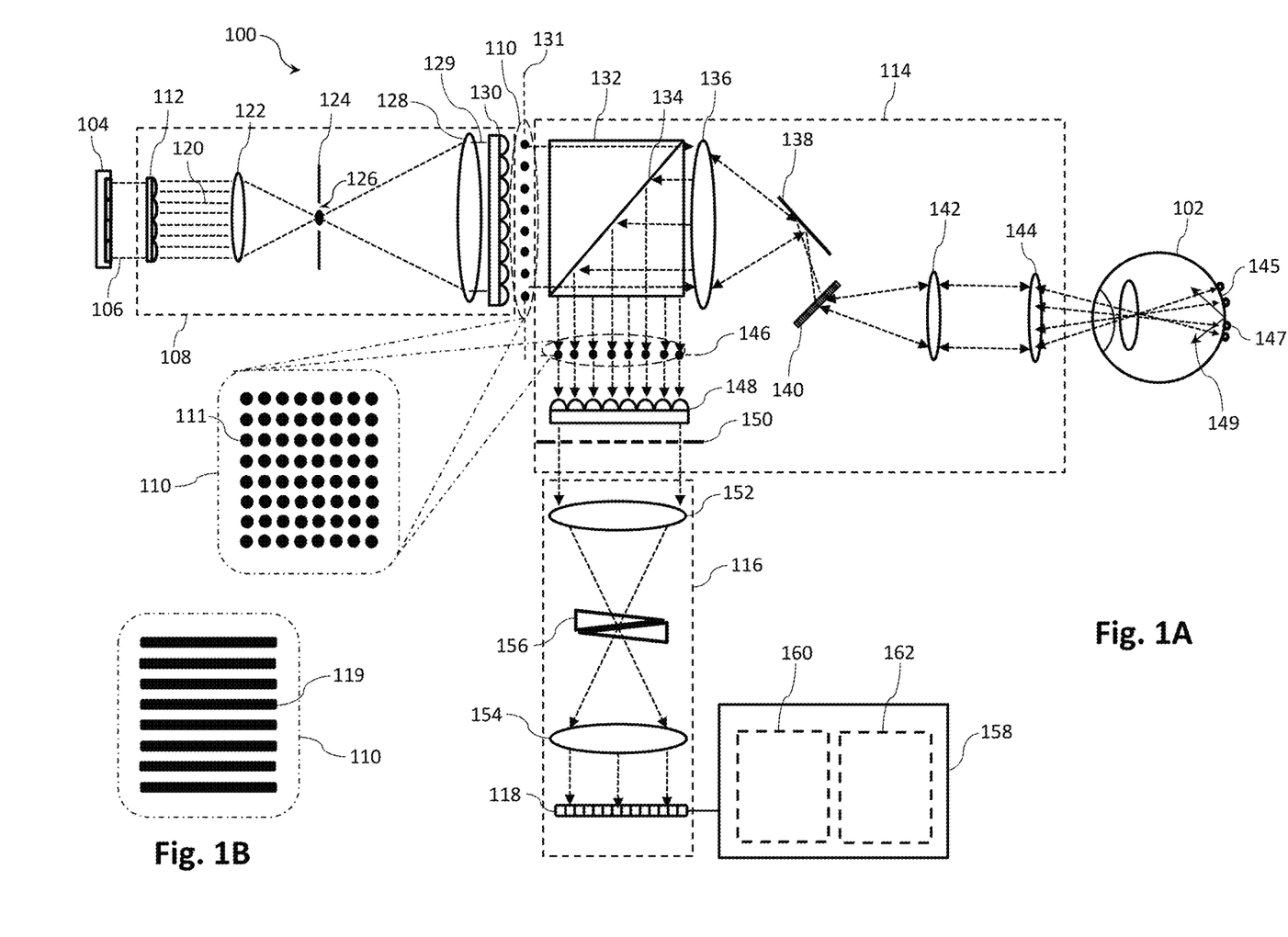
FIG. 1A is a schematic system level illustration of an apparatus for analyzing a sample in the form of a human eye according to a first embodiment of the invention.
FIG. 1B illustrates a variant structured illumination field produced by the FIG. 1A apparatus.

A first embodiment of the invention is illustrated schematically in FIG. 1A. With reference to this figure, there is illustrated an apparatus 100 for analyzing a sample in the form of a human eye 102. The apparatus 100 comprises a light source 104 configured to generate an input irradiance field 106 having a first wavelength band consisting of a plurality of wavelengths. In the arrangement illustrated, light source 104 comprises a spectrally broadband source in the form of a light emitting diode (LED), having low or no spatial coherence. In one embodiment, light source 104 includes an array of 16 substantially square emission areas arranged in a 4×4 configuration. However, in other embodiments, light source 104 may comprise an LED with a single emission area or arrays of LEDs. In alternative embodiments, light source 104 may comprise one or more highly spatially coherent sources such as superluminescent diodes or optical fiber-based supercontinuum sources.

In preferred embodiments, the optical source 104 emits visible light such that the first wavelength band lies in the visible region. However, in general, light in the near infrared (NIR), visible or UV spectral regions may be used depending on the particular application. Furthermore, optical source 104 may have spectral characteristics which include multiple spectral peaks. For example the source may comprise a white light phosphor LED source extending from 400 nm to 720 nm with intensity peaks at 450 nm and 550 nm.

The parameter of spatial coherence in terms of a light source can be defined as a single source that generates an irradiance field in which one contiguous area of the field is coherent with another area of the field at any point in time. Thus, a spatially incoherent source can be considered as a single light source that generates a contiguous irradiance field in which different areas of the field are not coherent at a point in time. In such light sources, light is emitted from different points across the surface of a single source independently and, thus, different points generate light having different phase relationships. Mathematically, the spatial coherence between two physical points is the cross-correlation between the two points over a period of time. Thus, incoherent light sources produce an irradiance field in which different points in the cross section of the irradiance field are uncorrelated (e.g. having a cross-correlation value of less than 0.1). Examples of spatially incoherent light sources include incandescent light bulbs, LEDs and arrays of LEDs laser or LED pumped phosphors, blackbody radiation and plasma light sources.

In preferred embodiments a structured light generator 108 converts the input irradiance field 106 into a structured illumination field 110 comprising a two-dimensional array of beamlets 111, illustrated in the inset of FIG. 1A. In an alternative embodiment the structured light generator 108 converts the input irradiance field 106 into a structured illumination field 110 comprising a one-dimensional array of linear beamlets 119, as shown in FIG. 1B. The operation of structured light generator 108 for the case of a spatially incoherent source is described in detail below. However, in alternative embodiments where the light source is spatially coherent, structured light generator 108 may be simplified to only include a focusing lens and a microlens array for example. Examples of spatially coherent light sources include SLEDs, single mode fiber ASE sources and supercontinuum white light generation in a single mode fiber, or swept wavelength diode lasers.

An optical system 114 is provided for projecting the structured illumination field 110 onto a region of the eye 102, such as a region of the retina 145. Optical system 114 includes optics configured to angularly encode the beamlets 111 such that each beamlet is projected onto a position, e.g. 147, of the eye 102 corresponding to the encoded angle. The components and operation of the optical system 114 are described in detail below.

Finally, apparatus 100 includes a spectrometer 116 comprising a two-dimensional sensor array 118 such as a CMOS camera for spectrally analyzing a portion of light 149 that is reflected, backscattered or fluoresced from the illuminated region of the eye 102. As is described below, spectrometer 116 is operatively associated with a processor 158 configured to generate a hyperspectral image comprising two or more en-face images of the illuminated region of the eye 102. The two or more en-face images include spectral response information of the sample from each beamlet 111 of the structured illumination field 110. In the context of the present invention, spectral response information includes one or more of: (1) reflected or backscattered chromatic spectral information from the illuminated region of eye 102 contained in reflected or backscattered beamlets; or (2) fluorescence spectral information emitted from the illuminated region of eye 102.

The term 'en-face image' is used in imaging applications such as Optical Coherence Tomography (OCT) to refer to a front-facing laterally resolved image of a sample. En-face images include a lateral image of a thin depth layer of a sample, where the data to produce the image may have been originally captured in two dimensions (e.g. using a Scanning Laser Ophthalmoscope) or three dimensions (e.g. in an OCT C-scan). An en-face image can also be an integrated view of multiple layers or surfaces as is often the case in OCT-Angiography. En-face imaging is contrasted with other imaging techniques such as 'A-scan' and 'B-scan' imaging, which relate to imaging a depth slice or slices of a sample in one or two dimensions.

Figure 2:
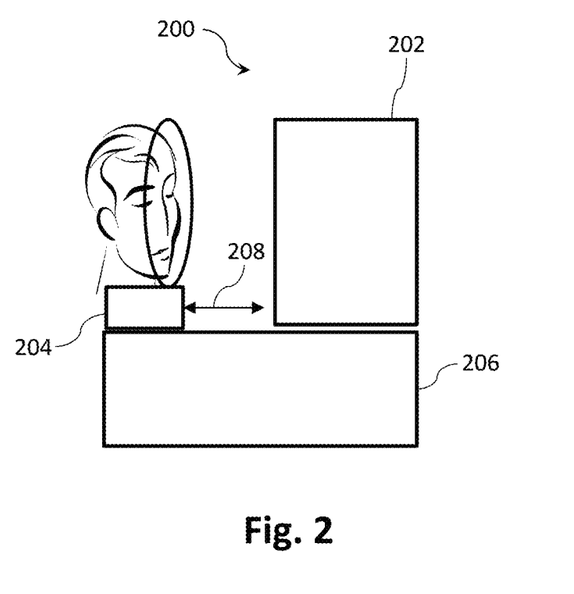
FIG. 2 is a schematic side view of an instrument configured to contain the apparatus of FIG. 1A.

Referring to FIG. 2, apparatus 100 is adapted to be incorporated into an instrument 200 for imaging a person's eye or eyes. Instrument 200 may include a main housing 202, which incorporates apparatus 100, a user support 204 for supportively maintaining a person's head during operation and a support base 206 for supporting instrument 200 on a surface. In some embodiments, housing 202 and user support 204 are able to be manually or electromechanically translated relative to each other as indicated by arrow 208.

Hyperspectral Dispersed Structured Illumination from a Spatially and Spectrally Incoherent Source Referring again to FIG. 1A, a first aspect of the present invention is the generation of hyperspectral dispersed structured illumination using a structured light generator 108. This allows for the use of a low-cost, spectrally broadband and spatially incoherent source such as an LED to generate a high density structured illumination pattern consisting for example of tens, hundreds or thousands of points or lines.

By way of example, light source 104 may be a low cost LED device comprising a 4×4 array of 16 blue LED emission areas on a pitch of 200 micron as provided by the Luxeon Z LED device sold by Lumileds Holding B.V. This device is capable of providing short pulse illumination exceeding 1 W of power at an excitation wavelength centered at around 425 micron, which can be additionally cascaded through dielectric filter multiplexing cubes if desired. The short pulse time provides for reducing motion artifacts during measurements. A lower duty cycle also provides capability for relatively high instantaneous peak powers but low average powers. The dielectric multiplexing cubes provide capability to combine more than one source.

Within the structured light generator 108, a two-dimensional array of beamlets 111 can be formed by a combination of optics now described. Initially, a beamlet generating device in the form of a first two-dimensional microlens array 112 is used to form the input irradiance field 106 into a plurality of co-propagating beamlets 120. Array 112 comprises a two-dimensional array of optical power elements in the form of substantially alike microlenses having a common focal length. The array of microlenses preferably matches the array of LEDs or emission areas in source 104 so that each LED or emission area has a corresponding microlens. These microlenses are preferably arranged into a substantially rectilinear array to match the LED array in source 104. However, it will be appreciated that the microlenses may be arranged into other types of arrays to match other arrays of LEDs. For example, microlens array 112 may be formed of crossed cylindrical microlens arrays of suitable numerical aperture. In an alternative embodiment, microlens array 112 may be replaced with micro beads such as that available from Nippon Electric Glass. These microbeads are able to be arranged onto a grid aperture and contacted directly to the LED light source.

Figure 3:
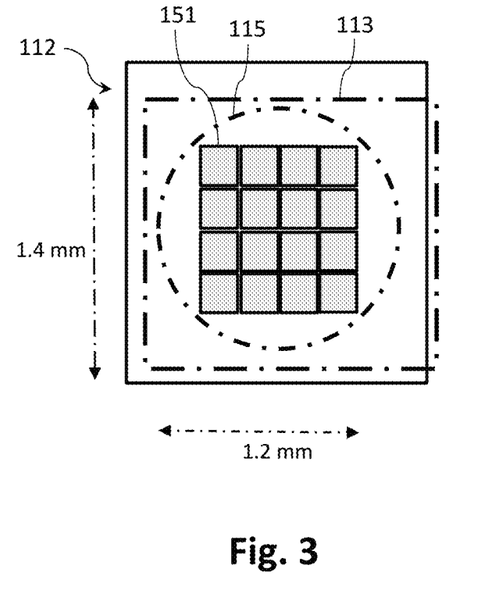
FIGS. 3 and 4 represent respectively plan and side views of a square array of 16 microlenses.
Figure 4:
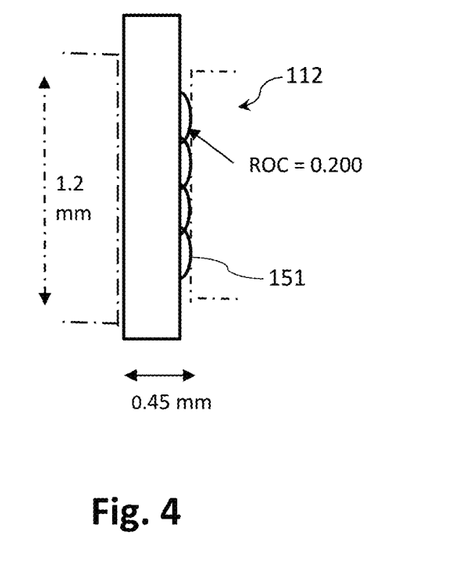

FIGS. 3 and 4 illustrate the geometry of an example 4 by 4 array 112 of square microlenses 151. The microlenses are disposed relative to each other having a 200 micron pitch. The thickness to the apex of each microlens 151 is about 0.450 mm and the radius of curvature of each microlens is about 0.200 mm. The overall substrate size may be variable, e.g. 1.6 mm by 1.6 mm, but there are keep out areas 113 extending to one edge on the plano side and a circular 1.2 mm keep out zone 115 at the height of the lens apex on the convex side of the optic that should be considered.

As described above, structured light generator 108 includes a first microlens array 112. Array 112 is positioned such that the input irradiance field 106 is incident onto the array of microlenses 151 to generate a two dimensional array of at least partially collimated initial beamlets 120.

The initial beamlets 120 are projected through a first optical power device in the form of a convergent lens 122 for spatially converging the at least partially collimated beamlets 120 to a predefined width at a convergence plane 124. Lens 122 may be a high numerical aperture lens, e.g. with numerical aperture in the range of 0.4 to 1.5, or a gradient index lens.

An aperture 126 may be disposed at the convergence plane 124 to limit the spatial extent of the LED output to allow a percentage of the generated light to pass and absorb or reflect back the remaining light, preferably for recirculation. Aperture 126 preferably has a diameter smaller than a diameter of the array of at least partially collimated beamlets 120 at the convergence plane. By way of example, the aperture 126 could be approximately 250 microns, thus permitting passage of light within a numerical aperture of 0.1 for a 1.25 mm focal length gradient index lens 122. In turn, the numerical aperture of the light emerging from aperture 126 will be approximately 0.4 mm/1.25 mm or 0.32 in each axis, assuming light source 104 is a 16 element LED array of fixed size. Here the 0.4 mm corresponds to the numerical aperture at aperture 126 due to the dimensions of the LED array 104 and lens 122.

A second optical power device in the form of an optical lens 128 is disposed at a distance equal to its focal length downstream from convergence plane 124. Lens 128 generates a near-collimated beam 129, in which an overall irradiance is a combination of individual irradiance fields from beamlets 120, which may be partially or fully overlapping. The numerical aperture of the near-collimated beam 129 may for example be 0.125 mm/25 mm or 0.005. The optical field at this point represents an expanded and at least partially overlapped form of beamlets 120 as modified by lenses 122 and 128 and aperture 126.

A second microlens array 130 having an extensive two-dimensional array of microlenses is positioned to receive the expanded beamlets output from lens 128 and form a two-dimensional array of imaging beamlets 111, which represent the structured illumination field 110 in a preferred embodiment. By way of example, the second microlens array 130 may include an array of 30×30 microlenses to form a grid of 900 imaging beamlets 111. Assuming each microlens of array 130 has a focal length of 1,000 microns, the second microlens array 130 takes the collection of beamlets in near-collimated beam 129 and generates a two-dimensional array of demagnified beamlets 111 which, at the focus, will have a demagnification of the 250 micron spot at aperture 126 by a factor of 1/25 to create an array of 10 micron images of the aperture 126, representing the structured illumination field 110.

The second microlens array 130 focuses the beamlets to a first focal plane 131 where the structured illumination field 110 is produced.

The Rayleigh diffraction limit for the microlenses of array 130 is less than but comparable with the aperture size, depending on the wavelength, so the aperture images will no longer be sharply resolved and the convolution of the 10 micron aperture images and the Rayleigh resolution will provide the structured illumination field 110 with a beamlet diameter slightly larger than 10 micron. This structured illumination field 110 can be used for various imaging applications such as those described below.

Hyperspectral Dispersed Illumination of a Sample to Extract Chromatic Spectral Information A second aspect of the present invention relates to hyperspectral structured confocal imaging of a sample to extract chromatic spectral information. This involves the simultaneous measurement of multiple wavelengths at a plurality of points on a sample to extract color or chromatic spectral information as a function of position across the sample.

Extending from the description above, and referring still to the embodiment illustrated in FIG. 1A, the structured illumination field 110 is projected through the optical system 114 onto the eye 102. System 114 includes an optical power splitting element in the form of a beamsplitter 132. Beamsplitter 132 is preferably formed of a partially reflective mirror 134 angled at about 45 degrees to the plane of the structured illumination field 110. The partially reflective mirror transmits a portion of the optical power and reflects the remaining optical power, which is coupled from the optical path and attenuated (not illustrated). The reflective properties of the mirror are chosen to be relatively uniform across the first wavelength band, with reflectivity selected so that a suitable level of power is incident onto the eye 102 for comfort and safety. It will be appreciated that, in other embodiments, beamsplitter 132 may include a polarization beamsplitter to selectively transmit only certain polarization components.

Where the light source 104 is sufficiently bright, the beamsplitter 132 may transmit approximately 20% of the incident optical power, thereby reducing the power input to the eye 102 to be within maximum permissible exposure limits for LEDs.

The fraction of light transmitted through beamsplitter 132 is projected onto a first collimating lens 136 that is preferably located at a distance equal to its focal length from the first focal plane 131. Lens 136 focuses the structured illumination field 110 onto a two-dimensional steering element 138 in the form of a micro-electromechanical mirror system (MEMS), which is located at the opposing focal plane of lens 136. Preferably, each of the beamlets 111 in the structured illumination field 110 is collimated to fill the MEMS 138, which may have a diameter of approximately 5 mm. MEMS 138 may comprise an electrically controllable mirror that is selectively rotatable in two dimensions by a connected controller (not illustrated) to translate the positioning of the structured illumination field 110 across different regions of eye 102.

The reflected and steered light from the MEMS element 138 is now dispersed angularly by a dispersive element 140 in the form of a transmissive diffraction grating. In some embodiments, grating 140 has a line density of 300 lines/mm and is configured to provide high efficiency coupling into a near Littrow angle over the first wavelength band. Grating 140 angularly disperses each of the beamlets 111 into an elongated band of spectral components corresponding to the plurality of wavelengths emitted by optical source 104. Thus, at this point, each beamlet is propagating with a distinct angle determined by its position in the array of beamlets 111 and each constituent wavelength of a beamlet is angularly dispersed at a unique angle. Described another way, each constituent wavelength component from source 104 will have a corresponding grid of beamlets, with each grid being offset in the dispersive axis of the grating 140.

It will be appreciated that, in alternative embodiments, diffraction grating 140 may be substituted with an alternative dispersive element such as a reflection grating or a prism.

The dispersed beamlets are then passed through an 8-f lens relay of lenses 142 and 144 and subsequently projected onto the eye 102. Lenses 142 and 144 represent a retinal lens arrangement which directs the structured illumination pattern towards eye 102. In this system, the eye 102 performs the angle to offset conversion to define a grid of beamlets on the retina 145. The action of the optical power elements of eye 102 is to focus the collimated beamlets to the retina 145 at positions 147 which correspond to their propagation angles. This angle and hence position on the retina is now uniquely determined by the position of the originating beamlet and the wavelength dispersive angle, i.e. the color of the spectral component. That is, the position 147 where each beamlet and wavelength component strikes the eye is dependent on both the original beamlet position in the array of beamlets 111 and the wavelength of the beamlet spectral component.

The retinal lens arrangement 142, 144 may include an electromechanical adjustment along the axial dimension to adjust the focal position in a manner similar to an autofocus technique.

Figure 5:
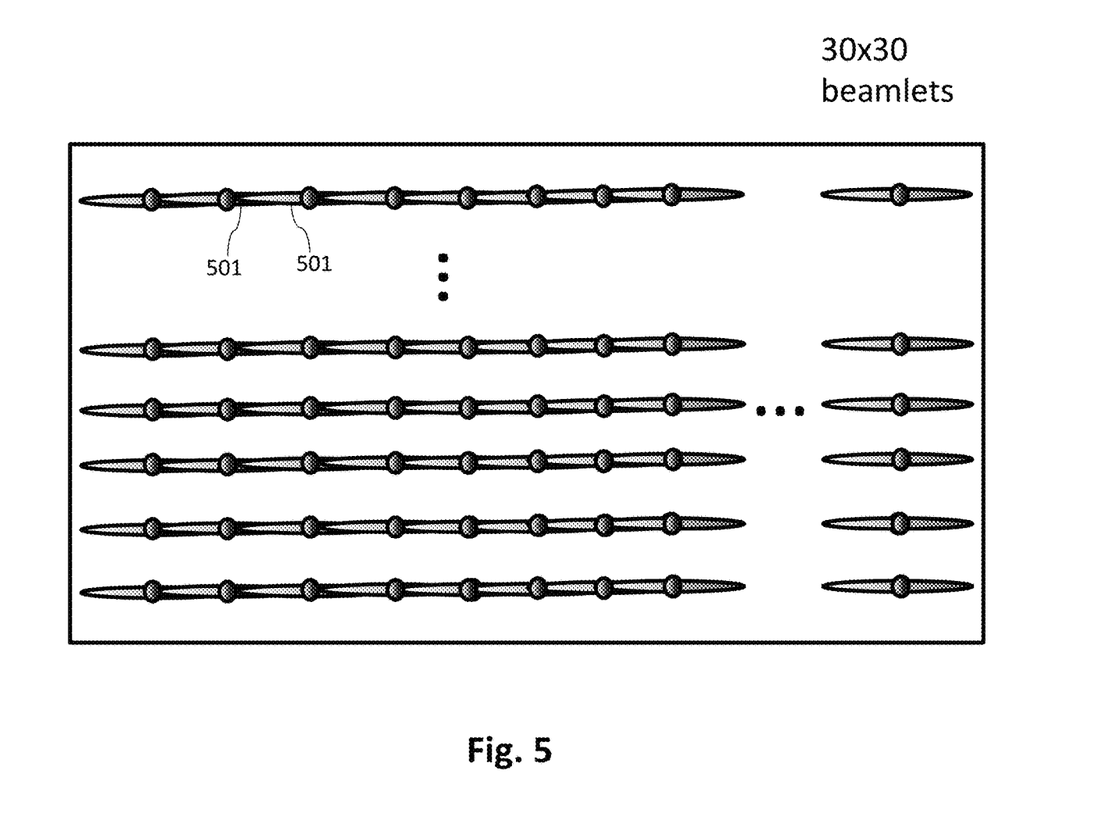
FIG. 5 is a schematic illustration of a grid of beamlets dispersed into beamlet bands that extend along an axis of the grid.

The dispersive angle of the beamlets with respect to the beamlet grid is determined by the orientation of microlens array 130 with respect to the dispersive axis of grating 140 and can be chosen to be in the direction of one of the axes of the beamlet grid as shown in FIG. 5. This allows the projection of a series of lines onto the retina and wherein, due to overlap of elongated beamlet bands 501, multiple positions on the retina 145 are illuminated by multiple wavelength components (colors) originating from different microlens locations within the microlens array 130. Thus, multiple wavelengths can be imaged by the spectrometer from each illuminated point in areas of overlap in the illuminated region of the sample to obtain chromatic spectral information.

Alternatively, the wavelength components can be dispersed at an angle relative to the axes of the beamlet grid 110. This results in a more uniform and lower intensity exposure of the retina, which can be helpful in reducing discomfort to a patient. In both cases, a complete image of the retina over multiple colors is obtained by dithering the MEMS 138 in two axes using a controller. A complete scan comprising a predetermined range of angles over the eye 102 allows each position within a selected region of the retina 145 to be illuminated by all wavelengths within a cycle of the dither.

The return path of light 149 reflected or back-scattered from the retina of eye 102 is now described.

The effect of the unaccommodated eye is to essentially act as a retro-reflector to return at least a portion of the light in each beamlet along the original beamlet trajectory. As such, the angular dispersion introduced on the forward path to the retina 145 is able to be reversed on the return path through lenses 144 and 142 and diffraction grating 140. The returned light is reflected from mirror 134 of beamsplitter 132 and the structured illumination field 110, including a grid of all-wavelength beamlets, is re-formed at a conjugate focal plane 146. Following the above example of beamsplitter 132 transmitting 20% of light from the optical source 104, 80% of the return light is reflected from beamsplitter 132 to plane 146 with only a small loss of power. At plane 146, each spectral component or color in a given beamlet represents the reflection coefficient of the retina 145 for that color at the position 147 on the retina to which it was mapped.

Thus, at plane 146, the returned light represents the incident structured illumination field 110 but with retinal reflection and chromatic spectral information encoded therein.

The returned light is then passed through a further microlens array 148 where each of the beamlets is collimated. The collimated beamlets are then passed through an aperture array 150 having a pitch corresponding to the two-dimensional array of beamlets. Aperture array 150 is positioned to confocally project the light that was collected from the illuminated region of the sample into spectrometer 116. In this manner, aperture array 150 spatially filters out peripheral and out of focus light from the beamlets in a confocal manner. The beamlets are then analyzed by spectrometer 116.

Figure 6:
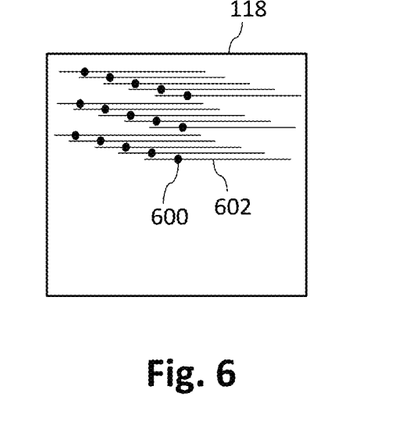
FIG. 6 is an example mapping of a two-dimensional grid of beamlets dispersed onto unique sets of pixels of a sensor array.

Spectrometer 116 includes a relay of lenses 152 and 154 disposed in a 4-f confocal configuration. First lens 152 spatially converges the beamlets to a point at a common focal length between lenses 152 and 154. A dispersive element 156 in the form of a wedge pair is situated at this common focal point and is configured to angularly disperse the wavelength components from each beamlet. Lens 154 images the angularly dispersed wavelength components onto two-dimensional sensor array 118. An example mapping of a two-dimensional grid of beamlets 600 dispersed onto unique sets of pixels 602 of the sensor array 118 is illustrated in FIG. 6. In other embodiments, wedge pair 156 may be replaced with an alternative dispersive element such as a transmissive or reflective diffraction grating or a prism.

Spectrometer 116 is operatively associated with a processor 158 which processes the sensor data to form en-face images of the eye for each wavelength component (color). To construct images, processor 158 includes a spectral mapping module 160 configured to map positions on the sensor array 118 to a two dimensional position on the sample 102 and a wavelength of the light (from each beamlet spectral component) within a plurality of predefined wavelength bins based on a predefined mapping function.

In this manner, the dispersed beamlet spectral components may be used for both position and spectral information. In these embodiments, the spectral mapping module 160 is configured to divide the wavelengths corresponding to the detected elongated bands of spectral components for each dispersed beamlet into wavelength bins. Wavelengths within a given wavelength bin are designated as originating from a common position on the sample 102 and therefore represent a spectral response for that retinal position. Wavelengths in different wavelength bins are designated as originating from different positions on the sample, e.g. spatially distinct retinal positions.

By way of example, the input first wavelength band from source 104 may extend over a bandwidth of 500 nm, which defines the size of each elongated band of beamlet spectral components. By dividing the 500 nm range into 100 bins of 5 nm, each beamlet can contribute 100 spatially distinct retinal points, each with 5 nm of spectral bandwidth. Thus, using an arrangement of only 30×30 beamlets, 90,000 different spatial points across the retina can be simultaneously imaged at multiple wavelengths. By adjusting the size of wavelength bins, the spectral bandwidth and spatial resolution of the images can be traded off.

Processor 158 also includes a hyperspectral image generator 162 configured to generate a hyperspectral image from sensor signals of sensor array 118 and the predefined mapping function of module 160. The generated hyperspectral image comprises two or more en-face images of the illuminated region of the eye, with each of the en-face images including spectral response information of the eye from each beamlet 111 of the structured illumination field 110. Thus, system 100 can image both spatially and spectrally in a simultaneous manner.

It will be appreciated that spectral mapping module 160 and hyperspectral image generator 162 represent functional elements of processor 158 that may be implemented as algorithms in software, hardware (e.g. CMOS) or a combination of both.

To image different regions across the retina 145, MEMS 138 is tilted by an electronic dither signal to translate the region of illumination laterally across the retina in two dimensions as described above. Thus, a full en-face image of a selected area of the retina 145 can be constructed for each wavelength within the first wavelength band. In this embodiment, the spectral response information that can be extracted from the retina includes a reflectance power spectrum corresponding to each retinal point within the selected area.

Due to the confocal nature of apparatus 100, only a narrow range of depths of a sample will be imaged during a two-dimensional angular scan of MEMS 138. To generate a three-dimensional image of the retina, the focus of the structured illumination field may be translated so as to focus at different retinal depths. To achieve this, optical system 114 preferably includes means for translating the focal plane of the structured illumination field 110 in the axial direction relative to the retina 145. In some embodiments, this translating means includes a manual or electromechanical adjustment mechanism or actuator for physically adjusting the position of system 100, embodied in instrument 200, relative to the eye 102. For example, as illustrated in FIG. 2, housing 202, which includes apparatus 100, and user support 204 are able to be manually or electromechanically translated relative to each other as indicated by arrow 208. For example, the user support 204 may be translated while the housing is maintained stationary. Alternatively, the housing 202 may be translated while the user support 204 is maintained stationary. The translation may be through a linear actuator disposed on support base 206. In other embodiments, optical system 114 may include a retinal lens and the focus of the retinal lens may include motorized stages or variable focus lenses which may be adjusted to select a different imaging depth.

This process is typically performed to initially set the desired imaging depth. To subsequently change the imaging depth, the axial position of one or more of lenses 142 and 144 are mechanically actuated by a linear or other actuator to adjust the focal position of the structured illumination field 110 onto eye 102. By way of example, the axial position of lens 144 may be linearly translated relative to lens 142 to adjust the focal position and therefore imaging depth within eye 102.

During the acquisition of a sequence of images, there can be some eye motion as the various frames are acquired, in addition to the intended translation of the illumination across the retina 145 at the different MEMs settings. Although each color bin provides only a sparse image of the retina, it is possible, based on the overall line scans to accurately co-register each of the image frames based on a color-averaged version of the image. In this process, color information is used as additional position information to overcome or at least reduce effects due to motion of the eye 102 during the image sequence. For each of the registered image frames the hyperspectral components corresponding to a given pixel location can be acquired. Through the dithering, i.e. translation of the imaging region by the MEMS 138, and oversampling a complete high pixel count hyperspectral image can be obtained once the number of frames is sufficiently high.

For many applications, this amount of information is overwhelming and may not be helpful in visualization of a particular retinal pathology and so simplification in processing the data can be applied. For example a simple true color image of the retina 145 can be provided by grouping the detected wavelength components into Red, Green and Blue (RGB) bands. Alternatively, narrow spectral regions can be summed with an appropriate summation or difference to provide a single value that can be represented in intensity or false color.

Apparatus 100 is able to be combined with a NIR OCT system, with OCT images able to be registered relative to confocal images obtained by apparatus 100. A somewhat similar system is described in published PCT patent application No WO 2018/000036 A1, to Steven James Frisken, entitled 'Apparatus and method for confocal microscopy using dispersed structured illumination' (hereinafter 'Frisken'), the contents of which are incorporated herein by way of cross-reference. However in the present embodiment, the confocal images obtained by apparatus 100 are now able to be separately processed into different spectral bands to provide a hyperspectral analysis of the retina which can help in the identification of spectral features. Hence, the present embodiment provides capability for diagnosing certain pathologies which may be identified or characterised through the chemical or molecular spectral signature of the retina, as opposed to or in addition to the structural information which is provided by a confocal image or an OCT image of the retina.

In some embodiments, the 8-f retinal lens relay 142, 144 illustrated in FIG. 1A may be replaced with an anterior lens arrangement configured to project the angle-encoded beamlets from MEMS 138 onto multiple locations on one or more anterior regions of eye 102 such as the cornea or lens.

Structured White Light Illumination of a Sample to Extract Chromatic and Fluorescence Spectral Information A third aspect of the present invention involves illumination of a sample with white light and provides for obtaining both reflected or backscattered chromatic spectral information as well as fluorescence spectral information from the sample. An apparatus 700 according to a second embodiment is illustrated schematically in FIG. 7. Apparatus 700 includes many elements that are common to apparatus 100 and these common elements are designated with the same reference numerals for simplicity.

Figure 7:
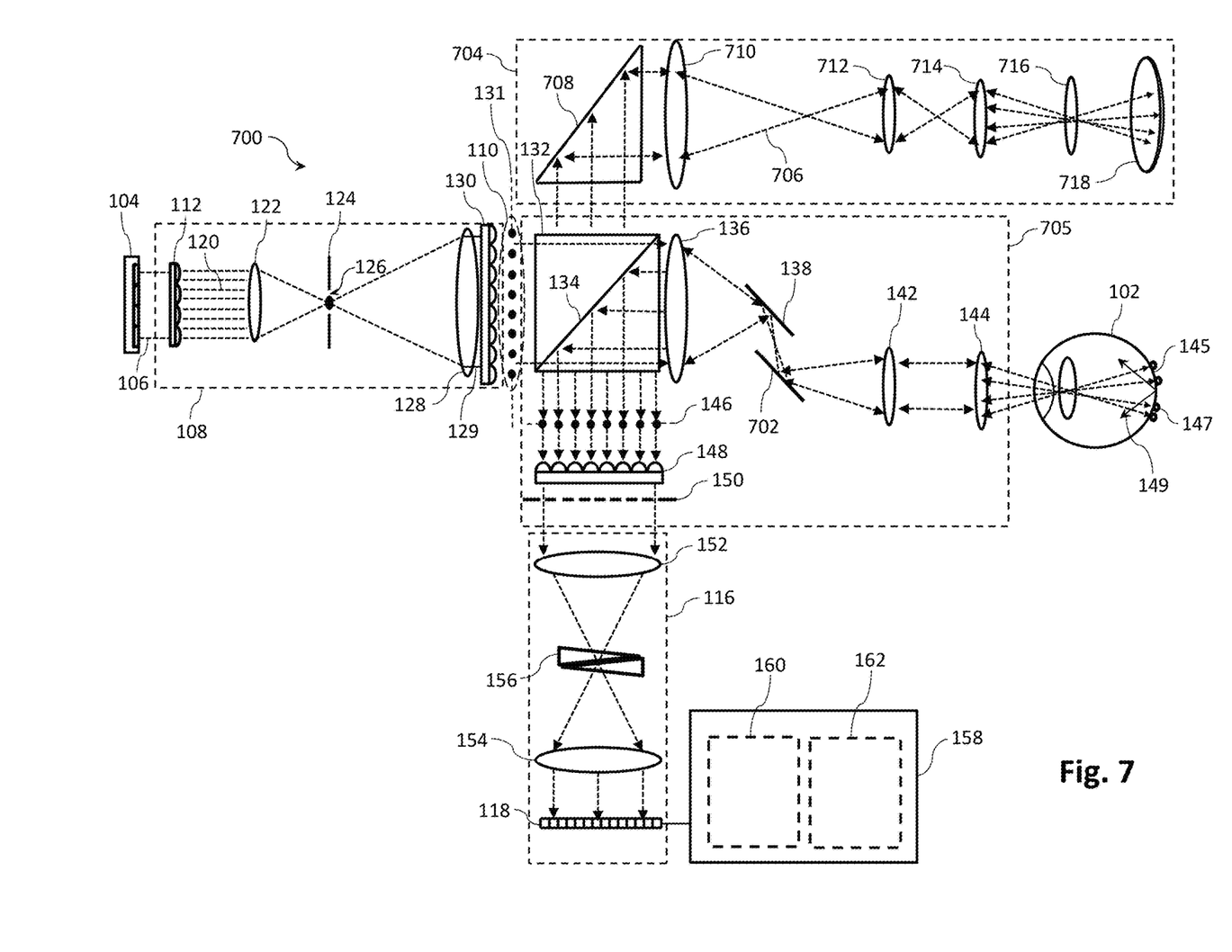
FIG. 7 is a schematic system level illustration of an apparatus for analyzing a human eye according to a second embodiment of the invention.

Illumination in apparatus 700 is provided by a light source 104 that is spectrally broadband so as to illuminate a sample such as an eye 102 with 'white light' having wavelengths extending substantially across the entire visible and NIR wavelength range. By way of example, light source 104 may comprise an LED, an array of LEDs or a superluminescent diode in which the range of wavelengths emitted covers several hundred nanometers in the visible and NIR spectral regions. Thus, the same or similar light sources may be used for both the first and second embodiments. The light source may be spatially incoherent or spatially coherent. As in FIG. 1A, the apparatus is illustrated with spatially incoherent light source 104 and a structured light generator 108 for providing the structured illumination field 110.

The primary difference between apparatus 100 and apparatus 700 is the replacement of diffraction grating 140 with a non-dispersive optical directing element 702 such as a mirror in a primary sample path 705. Mirror 702 acts to directly reflect all beamlets without dispersion of constituent wavelength components so that all wavelengths co-propagate together along path 705 to eye 102. This results in eye 102 being illuminated by a grid of 'white light' beamlets with each beamlet including all of the wavelengths emitted by light source 104. This provides a more concentrated illumination onto the retina 145 than with the dispersed beamlets of apparatus 100, so light source 104 is typically operated at a lower intensity than in apparatus 100 for improved safety and patient comfort.

The remaining operation of apparatus 700 is substantially similar to that of apparatus 100, with each returning beamlet being confocally imaged by aperture array 150 and spectrometer 116. The decoupling of the illumination source from the spectrum of the measured reflected light enables additional information about the eye to be extracted. For example, sensor array 118 is now capable of simultaneously detecting, as spectral response information, both the reflectance spectra and also any fluorescence spectra due to autofluorescence in the eye tissue. This is possible as the fluorescence spectra are detected at different wavelengths from the excitation spectra and, absent any controlled dispersion of the beamlets from dedicated dispersive optical elements, the fluorescence can be distinguished.

Apparatus 700 may optionally include a reference arm 704 for performing OCT. In this embodiment, beamsplitter 132 operates as a power splitting element configured to direct a portion, referred to as the reference light 706, of the optical power of the structured illumination field 110 along reference arm 704 and the remainder of the optical power of the structured illumination field to the eye 102.

In the illustrated embodiment, reference arm 704 includes a reflective element 708 such as a prism or a mirror for guiding the reference light 706 along the reference arm 704. The reference arm 704 further includes a lens relay comprising lenses 710, 712, 714 and 716 for substantially matching the path length of the primary sample path 705, including the optical power elements of the eye 102. A reflective element in the form of a curved metallic reflector 718 is provided for reflecting the light back along the reference arm 704 to be recombined with light returning from the sample 102 at beamsplitter 132. Preferably the properties of lens 716 and reflector 718 in combination are defined such that they substantially match the dispersive properties of eye 102. It will be appreciated that the number, type and position of optical elements in reference arm 704 may differ substantially in different designs provided that the collective effect is to substantially match the path length and dispersive properties of the primary sample path 705.

The inclusion of reference arm 704 allows for performing coherence gating of the received signal for a more axially localized examination of the eye 102. This form of full color OCT can be used to localize the hyperspectral signal to an axial region of interest. To keep the system reasonably simple, the spectrum of the input irradiance field 106 detected on the 2-D sensor array 118 may be divided into a plurality of wavelength bins (e.g. 100 bins) with each bin having a defined spectral width (e.g. 5 nm). Within each wavelength bin, a subset of individual wavelengths (e.g. 32 wavelength points) can be used as coherence gates as in OCT on which a Fast Fourier Transform (FFT) can be performed to obtain structural (depth) information for each spectral band. These FFTs can be performed to provide a range of axial positions across the sample to build up a plurality of hyperspectral images with each image including the whole two dimensional map across a whole color range.

By limiting the requirements on the OCT range and resolution, the apparatus can be kept relatively simple without requiring highly accurate dispersion compensation over an extended wavelength range. That is, the dispersion only needs to be compensated within a single hyperspectral wavelength bin.

In some embodiments, the length of reference arm 704 may be selectively adjustable to select a wavelength of coherence to be imaged by the spectrometer. This may be achieved by an actuator mechanism to mechanically translate reflector 718 and/or other optical elements in the reference arm 704. In one embodiment, the means for adjusting the reference path length is the same mechanism as the means for translating the focal plane of the primary sample path 705 to different sample depths.

Thus, the depth within an eye 102 being analyzed can be varied by adjusting the position of the instrument 700 relative to the eye 102. If a retinal lens 142, 144 is present, the focal position of the retinal lens can be adjusted to simultaneously select both the confocal gating and the coherence gating and provide a hyperspectral mapping of the retinal layers. Where the presence of an absorption or scattering feature is being sought, spectral difference techniques can be applied to the different axial layers. For example, wavelength bins may be differenced to produce information on blood oximetry of the eye 102.

In some embodiments, apparatus 100 and apparatus 700 may be incorporated into a single instrument, with the functionality of both apparatus being able to be used in conjunction with one another. For example, in some embodiments, diffraction grating 140 is interchangeable with mirror 702. This interchangeability is able to be effected by mechanically moving, by an actuator, the diffraction grating 140 and mirror 702 into or out of the optical path as necessary. This may be performed by a linear actuator or the like controlled by an external controller or processor 158.

In some embodiments, system 700 may utilize an eye tracker and/or retinal camera to accurately register the position on the eye currently being imaged. This allows for accurate position registration of light incident onto different regions of sensor array 118.

Hyperspectral Fluorescence Imaging of a Sample

Figure 8:
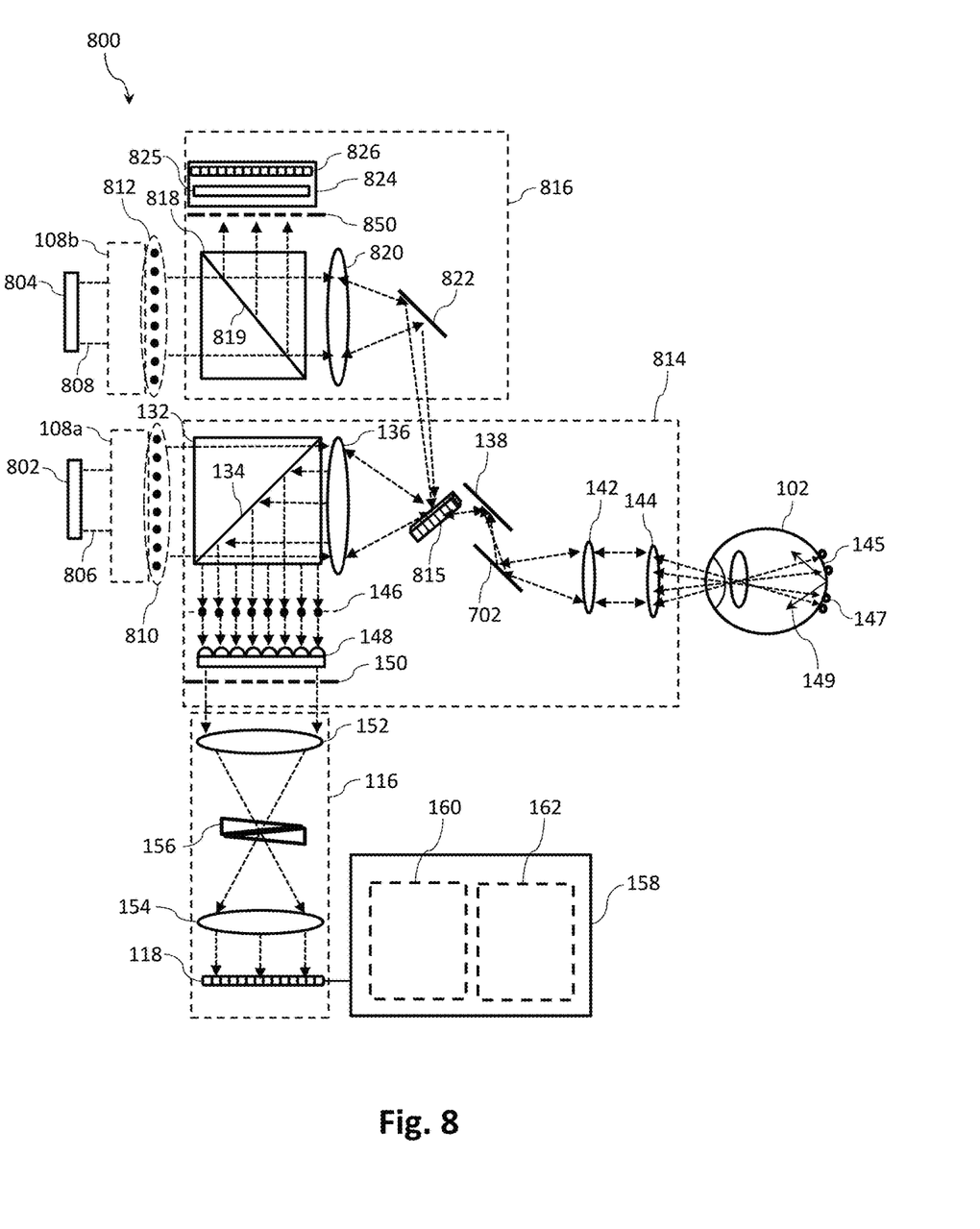
FIG. 8 is a schematic system level illustration of an apparatus for analyzing a human eye according to a third embodiment of the invention.

A third embodiment of the present invention is illustrated as apparatus 800 in FIG. 8. Apparatus 800 provides hyperspectral fluorescence imaging of a sample such as an eye 102 with accurate position registration to account for ocular movements. This functionality represents a fourth aspect of the present invention. Apparatus 800 includes many elements common to apparatus 100 and 700 and these common elements are designated with the same reference numerals for simplicity.

Apparatus 800 includes two light sources 802 and 804 configured to generate respective input optical beams 806 and 808. Similar to FIGS. 1A and 7, both light sources 802 and 804 are spatially incoherent and have structured light generators 108a and 108b, as described above, to generate structured illumination fields 810 and 812 respectively. However, it will be appreciated that apparatus 800 may employ spatially coherent light sources such as SLEDs or supercontinuum sources.

Light source 802 is configured to provide a beam 806 in the ultraviolet or visible wavelength range and preferably in one of the UVA, violet, blue or green wavelength ranges, which will be referred to as 'colored light'. Light source 804 is configured to provide a beam 808 in the NIR wavelength range, which will be referred to as 'NIR light'.

In an alternative embodiment, the different wavelength bands of beams 806 and 808 are obtained from a single optical source using wavelength-selective optics such as a diffractive element, an optical filter or bulk optics dichroic splitter.

Structured colored light illumination field 810 from source 802 is passed through a primary imaging path 814, which includes beamsplitter 132, lens 136, MEMS 138, mirror 702 and lenses 142 and 144 as described previously. Primary imaging path 814 also includes a diffractive multiplexing element in the form of a volume phase grating 815, the operation of which is described below. In other embodiments, volume phase grating 815 may be replaced with a dichroic mirror and a conventional diffraction grating.

Simultaneously, NIR light structured illumination field 812 from source 804 is passed through a secondary path 816. Path 816 includes a beamsplitter 818, focusing lens 820 and mirror 822 to couple the NIR light onto volume phase grating 815. Beamsplitter 818 includes a partially reflective mirror 819 and has properties similar to beamsplitter 132 described above. Beamsplitter 818 serves to direct NIR light that is scattered or back reflected into secondary path 816 to a spectrometer 824 for spectral analysis in a similar manner to spectrometer 116. Spectrometer 824 has a corresponding sensor array 826, which is operatively associated with processor 158 (connection not shown). Spectrometer 824 also includes a dispersive system 825, similar to that of spectrometer 116.

Both the colored structured illumination field 810 and NIR structured illumination field 812 are focused to a confined region on volume phase grating 815. Volume phase grating 815 is configured both to multiplex the light from fields 810 and 812 together and to spatially disperse the NIR wavelengths from NIR field 812. All wavelengths of colored structured light illumination field 810 are transmitted through volume phase grating 815 in a spatially confined (non-dispersed) state. This is achieved by configuring volume phase grating 815 such that the beamlets of NIR field 812 are incident on the grating at an angle that ensures a first diffractive order is coupled along primary imaging path 814. At the same time, the beamlets of colored structured illumination field 810 should be incident onto volume phase grating 815 at an angle that ensures that the zeroth diffractive order, comprising all wavelengths co-located, is coupled along primary imaging path 814.

After transmission through volume phase grating 815, the NIR field 812 comprises a dispersed grid of beamlets that are elongated in the dispersion axis of the volume phase grating 815. Described differently, after being dispersed by volume phase grating 815 the NIR field 812 comprises a plurality of angularly encoded co-propagating grids of beamlets of different wavelengths, wherein each grid has a propagation angle dependent on its wavelength. Colored structured light illumination field 810 is substantially unmodified by volume phase grating 815 and comprises light from all wavelengths within the colored band emitted by light source 802 (e.g. UVA, violet, blue or green). Thus, all wavelengths within colored field 810 co-propagate along the same trajectory as a single grid of beamlets.

The co-propagating color and NIR structured illumination fields 810 and 812 are projected onto eye 102 and imaged at a plurality of positions 147 on retina 145. Upon incidence onto retina 145, the beamlets of the color structured illumination field 810 are encoded with fluorescence information from retina 145 due to autofluorescence from certain molecules.

Upon reflection, back-scatter or fluorescence 149 from retina 145, the structured illumination fields 810, 812 are passed back along primary imaging path 814 to volume phase grating 815. The color structured illumination field 810 and generated fluorescence pass back through volume phase grating 815 without dispersion, then are reflected from mirror 134 of beamsplitter 132 and passed through aperture array 150 for confocal gating before being detected by grid spectrometer 116. Confocal gating is important in fluorescence imaging to reject light that is not related to the part of the sample (in terms of depth) under test. In the case of imaging eyes for example, fluorescence or backscatter from the cornea or aqueous humor of the eye can provide a strong signal which is preferably removed so as to achieve a stronger signal to noise ratio for the fluorescence signal from the retina 145.

The dispersion of light in NIR structured illumination field 812 that is reflected or backscattered from retina 145 is reversed upon passing back through volume phase grating 815. The recovered NIR beamlets then return along secondary path 816 where they are spatially filtered with an appropriately sized aperture array 850 and imaged or analyzed at spectrometer 824, which includes a dispersive element 825 and a sensor array 826.

The sensor array 118 of spectrometer 116 receives the grid of colored beamlets from first light source 802, which are dispersed according to wavelength by dispersive wedge pair 156. Thus, spectral information can be obtained for each grid point on the sample, which includes fluorescence spectral information due to local molecules at that position and depth.

Simultaneously, sensor array 826 receives a grid of NIR beamlets dispersed by dispersive element 825. Processor 158 processes the signal received at sensor array 826 to generate spectral mapping information. This information provides for position registration of the sensor locations to positions on the retina 145 as processor 158 is able to apply a mapping function to map the trajectories of the dispersed NIR wavelengths. The known positions can be used to reference the fluorescence spectra measured at sensor 118 to the retinal locations to provide an accurate mapping and reduce motion blur artifacts.

From the above process, apparatus 800 can produce a two-dimensional fluorescence spectrogram of a particular region and layer of eye 102. Apparatus 800 can be used to image different regions of eye 102 by mechanically tilting MEMS 138 in the manner described above. Different depths of eye 102 can be imaged by mechanically translating apparatus 800 relative to a patient in the manner described above. By imaging different lateral regions and depths, a three-dimensional fluorescence spectrogram of eye 102 can be produced.

In preferred embodiments the structured illumination field 110 comprises a two-dimensional array of beamlets 111, as shown in FIG. 1A. However in alternative embodiments the structured illumination field 110 comprises a one-dimensional array of linear beamlets 119 as shown in FIG. 1B. With reference to FIG. 1A, this form of structured illumination field can be produced by replacing the two-dimensional microlens array 130 with an array of cylindrical microlenses. In other modifications the returning linear beamlets are passed through a microlens array 148 comprising an array of cylindrical microlenses to collimate them in the short axis, and the collimated beamlets are then passed through an array 150 of linear apertures having a pitch corresponding to the one-dimensional array of linear beamlets. The spatially filtered returning beamlets then pass to the spectrometer 116 for spectral analysis as described previously. The apparatus described with reference to FIGS. 7 and 8 can be modified in analogous fashion.

CONCLUSIONS

It will be appreciated that the invention described above provides capability to simultaneously image chromatic or fluorescence spectral information from a sample at a plurality of points. The invention is able to be operated in different modes to obtain different spectral information from a sample including full field color spectral information and fluorescence spectral information. The invention is also able to incorporate an OCT system if necessary.

Embodiments of the invention provide a highly efficient retinal confocal imaging system that is capable of quickly capturing a fluorescence spectrum with sufficient resolution and across a large field of view to be suitable for screening and disease diagnostics. Further embodiments (not illustrated) are capable of performing the above as a function of the excitation wavelength by selectively varying the wavelength of the input light source.

The fluorescence information obtained from an eye by the inventive apparatus and methods can be useful in identifying important information related to the aging and health of the RPE layer and hence the photoreceptors. The fluorescence information can also be used to diagnose the onset of Alzheimer's disease in patients.

Interpretation

It will be understood by one skilled in the art that the frequency and wavelength of a laser beam are connected by the equation:

Speed of light=wavelength*frequency.

As a consequence, when reference is made to terms such as wavelength band, wavelength dispersion, wavelength dependence and similar terms, these are interchangeable with the corresponding terms frequency band, frequency dispersion and frequency dependence and the like.

It will be appreciated that various optical elements described as lenses, prisms or mirrors may be interchangeable with corresponding optical power elements to produce the same overall effect (focusing, converging, collimating etc.). For example, a lens may be replaced with a reflective mirror, prism or relay of optical elements with collective equivalent optical effects to the lens. Similarly, one dispersive element such as a diffraction grating may be substituted for another dispersive element such as a prism to perform an equivalent dispersive operation.

Throughout this specification, use of the term 'element' is intended to mean either a single unitary component or a collection of components that combine to perform a specific function or purpose.

Unless specifically stated otherwise, as apparent from the following discussions, it is appreciated that throughout the specification discussions utilizing terms such as 'processing', 'computing', 'calculating', 'determining', 'analyzing' or the like, refer to the action and/or processes of a computer or computing system, or similar electronic computing device, that manipulate and/or transform data represented as physical, such as electronic, quantities into other data similarly represented as physical quantities.

In a similar manner, the terms 'controller' or 'processor' may refer to any device or portion of a device that processes electronic data, e.g. from registers and/or memory to transform that electronic data into other electronic data that, e.g., may be stored in registers and/or memory. A 'computer' or a 'computing machine' or a 'computing platform' may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions, sequential or otherwise, that specify actions to be taken are included. Thus, one example is a typical processing system that includes one or more processors. Each processor may include one or more of a CPU, a graphics processing unit, or a programmable DSP unit. The processing system further may include a memory subsystem including main RAM and/or a static RAM, and/or ROM. A bus subsystem may be included for communicating between the components. The processing system further may be a distributed processing system with processors coupled by a network. If the processing system requires a display, such a display may be included, e.g., a liquid crystal display (LCD) or a cathode ray tube (CRT) display. If manual data entry is required, the processing system also includes an input device such as one or more of an alphanumeric input unit such as a keyboard, a pointing control device such as a mouse, and so forth. The term memory unit as used herein, if clear from the context and unless explicitly stated otherwise, also encompasses a storage system such as a disk drive unit. The processing system in some configurations may include a sound output device, and a network interface device. The memory subsystem thus includes a computer-readable carrier medium that carries computer-readable code, e.g. software, including a set of instructions to cause performing, when executed by one or more processors, one of more of the methods described herein. Note that when the method includes several elements, e.g. several steps, no ordering of such elements is implied unless specifically stated. The software may reside in the hard disk, or may also reside, completely or at least partially, within the RAM and/or within the processor during execution thereof by the computer system. Thus, the memory and the processor also constitute a computer-readable carrier medium carrying computer-readable code.

Reference throughout this specification to 'one embodiment', 'some embodiments' or 'an embodiment' means that a particular feature, structure or characteristic described in connection with the embodiment is included in at least one embodiment of the present disclosure. Thus, appearances of the phrases 'in one embodiment', 'in some embodiments' or 'in an embodiment' in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives 'first', 'second', 'third', etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms 'comprising', 'comprised of' or 'which comprises' is an open term that means including at least the elements/features that follow, but not excluding others. Thus, the term 'comprising', when used in the claims, should not be interpreted as being limitative to the means or elements or steps listed thereafter. For example, the scope of the expression 'a device comprising A and B' should not be limited to devices consisting only of elements A and B. Any one of the terms 'including' or 'which includes' or 'that includes' as used herein is also an open term that also means including at least the elements/features that follow the term, but not excluding others. Thus, 'including' is synonymous with and means 'comprising'.

It should be appreciated that in the above description of exemplary embodiments of the disclosure, various features of the disclosure are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claims require more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Similarly, it is to be noticed that the term 'coupled', when used in the claims, should not be interpreted as being limited to direct connections only. The terms 'coupled' and 'connected', along with their derivatives, may be used. It should be understood that these terms are not intended as synonyms for each other. Thus, the scope of the expression 'a device A coupled to a device B' should not be limited to devices or systems wherein an output of device A is directly connected to an input of device B. It means that there exists a path between an output of A and an input of B which may be a path including other devices or means. 'Coupled' may mean that two or more elements are either in direct physical, electrical or optical contact, or that two or more elements are not in direct contact with each other but yet still co-operate or interact with each other.

Thus, while there has been described what are believed to be the preferred embodiments of the disclosure, those skilled in the art will recognize that other and further modifications may be made thereto without departing from the spirit of the disclosure, and it is intended to claim all such changes and modifications as fall within the scope of the disclosure. For example, any formulas given above are merely representative of procedures that may be used. Functionality may be added or deleted from the block diagrams and operations may be interchanged among functional blocks. Steps may be added or deleted to methods described within the scope of the present disclosure.

I claim:

1. An apparatus for analyzing a sample, the apparatus comprising:
 a light source configured to generate an input irradiance field having a wavelength band consisting of a plurality of wavelengths;
 a structured light generator for converting the input irradiance field into a structured illumination field comprising an array of beamlets;
 an optical system for projecting the structured illumination field onto a region of the sample, including angularly encoding the beamlets such that each beamlet is projected onto a position of the sample corresponding to the encoded angle, wherein the optical system includes a dispersive element for angularly dispersing each of the beamlets into an elongated band of beamlet spectral components corresponding to each of the plurality of wavelengths, and for reversing, for a portion of light that is reflected or backscattered from the region of the sample, the angular dispersion applied to the beamlets;
 a spectrometer comprising a two-dimensional sensor array configured to spectrally analyze the portion of light that is reflected or backscattered from the region of the sample; and
 a processor operatively associated with the spectrometer, the processor including:
  a spectral mapping module configured to map, based on a predefined mapping function, positions on the sensor array to a two-dimensional position on the sample and a wavelength of the light within a plurality of predefined wavelength bins; and
  a hyperspectral image generator configured to generate a hyperspectral image from sensor signals of the sensor array and the predefined mapping function, the hyperspectral image comprising spectral response information of the sample from each beamlet of the structured illumination field.

2. The apparatus according to claim 1, wherein said structured light generator is configured to convert the input irradiance field into a structured illumination field comprising a two-dimensional array of beamlets.

3. The apparatus according to claim 1, wherein the light source is spatially incoherent.

4. The apparatus according to claim 1, wherein the optical system includes means for translating the structured illumination field relative to the sample.

5. The apparatus according to claim 1, wherein the optical system includes a lens relay disposed, in use, between the dispersive element and the sample to project the beamlet spectral components onto the sample at a position that is dependent on both the original beamlet position in the array of beamlets and the wavelength of the beamlet spectral component.

6. The apparatus according to claim 1, wherein the processor is configured to divide the wavelengths corresponding to the elongated band of beamlet spectral components into the wavelength bins, wherein wavelengths within a wavelength bin are designated as originating from a common position on the sample and wavelengths of different wavelength bins are designated as originating from different positions on the sample.

7. The apparatus according to claim 3, wherein the structured light generator includes a beamlet generating device having a two-dimensional array of optical power elements, the beamlet generating device being positioned such that, in use, the input irradiance field is incident onto the array of optical power elements to generate a two-dimensional array of at least partially collimated beamlets.

8. The apparatus according to claim 1, wherein the apparatus includes an aperture array positioned to confocally project the light that is reflected, backscattered or fluoresced from the region of the sample into the spectrometer, the aperture array having a pitch corresponding to the array of beamlets.

9. The apparatus according to claim 1, wherein the light source is configured to generate an input irradiance field having a plurality of wavelength bands, each consisting of a corresponding plurality of wavelengths.

10. The apparatus according to claim 9, wherein the optical system includes a multiplexing element for multiplexing the plurality of wavelength bands together.

11. The apparatus according to claim 1, wherein the apparatus includes a reference arm and a power splitting element configured to direct a portion of the optical power of the structured illumination field along the reference arm and the remainder of the optical power of the structured illumination field to the sample.

12. The apparatus according to claim 1, wherein said apparatus is configured for analyzing a sample comprising an eye.

13. A method of analyzing a sample, the method comprising the steps of:
 generating, from an input irradiance field having a wavelength band consisting of a plurality of wavelengths, a structured illumination field comprising an array of beamlets;
 angularly dispersing each of the beamlets into an elongated band of beamlet spectral components corresponding to each of the plurality of wavelengths;
 projecting the dispersed structured illumination field onto a region of the sample, including angularly encoding the beamlets such that each beamlet is projected onto a position of the sample corresponding to the encoded angle;
 reversing, for a portion of light that is reflected or backscattered from the region of the sample, the angular dispersion applied to the beamlets; and
 spectrally analyzing the portion of the light that is reflected or backscattered from the region of the sample using a two-dimensional sensor array, the spectral analyzing including:
  mapping, based on a predefined mapping function, positions on the sensor array to a two-dimensional position on the sample and a wavelength of the light within a plurality of predefined wavelength bins; and
  generating a hyperspectral image from sensor signals of the sensor array and the predefined mapping function, the hyperspectral image comprising spectral response information of the sample from each beamlet of the structured illumination field.

14. The method according to claim 13, wherein said structured illumination field comprises a two-dimensional array of beamlets.

15. An article of manufacture comprising a computer usable medium having a computer readable program code configured to operate the apparatus of claim 1.

16. An article of manufacture comprising a computer usable medium having a computer readable program code configured to implement the method of claim 13.

* * * * *